(12) United States Patent
Leibowitch

(10) Patent No.: US 9,101,633 B2
(45) Date of Patent: Aug. 11, 2015

(54) QUADRUPLE THERAPY USEFUL FOR TREATING PERSONS AFFLICTED WITH THE HUMAN IMMUNODEFICIENCY VIRUS (HIV)

(75) Inventor: Jacques Leibowitch, Paris (FR)

(73) Assignee: THE UNIVERSITY OF VERSAILLES SAINT-QUENTIN-EN-YVELINES, Versailles Cedex (FR)

( * ) Notice: Subject to any disclaimer, the term of this patent is extended or adjusted under 35 U.S.C. 154(b) by 188 days.

(21) Appl. No.: 13/511,013

(22) PCT Filed: Nov. 19, 2010

(86) PCT No.: PCT/EP2010/067853
§ 371 (c)(1),
(2), (4) Date: Jun. 19, 2012

(87) PCT Pub. No.: WO2011/061303
PCT Pub. Date: May 26, 2011

(65) Prior Publication Data
US 2012/0270828 A1  Oct. 25, 2012

(30) Foreign Application Priority Data
Nov. 20, 2009  (EP) .................................... 09176661

(51) Int. Cl.
| *A61K 31/7076* | (2006.01) |
| *A61P 31/18* | (2006.01) |
| *A61K 31/52* | (2006.01) |
| *A61K 31/505* | (2006.01) |
| *A61K 31/513* | (2006.01) |
| *A61K 31/536* | (2006.01) |
| *A61K 31/551* | (2006.01) |
| *A61K 31/675* | (2006.01) |
| *A61K 31/7068* | (2006.01) |

(52) U.S. Cl.
CPC .............. *A61K 31/52* (2013.01); *A61K 31/505* (2013.01); *A61K 31/513* (2013.01); *A61K 31/536* (2013.01); *A61K 31/551* (2013.01); *A61K 31/675* (2013.01); *A61K 31/7068* (2013.01)

(58) Field of Classification Search
None
See application file for complete search history.

(56) References Cited

U.S. PATENT DOCUMENTS
2012/0283177 A1  11/2012 Leibowitch

FOREIGN PATENT DOCUMENTS
WO  2011/061302  5/2011

OTHER PUBLICATIONS

Pinheiro et al. Antiviral Research 79 (2008) 143-165.*
Cohen et al., "Pilot Study of a Novel Short-Cycle Antiretroviral Treatment Interruption Strategy: 48-Week Results of the Five-Days-On, Two-Days-Off (FOTO) Study", 8(1):19-23 (2007).
Ferrer et al., "Zidovudine/Lamivudine/Adacavir Plus Tenofovir in HIV-Infected Naive Patients: A 96-Week Prospective One-Arm Pilot Study", AIDS Res Hum Retroviruses, 24(7):931-934 (2008).
Erik De Clercq, "The History of Antiretrovirals: Key Discoveries over the Past 25 Years", Rev Med Virol 19:287-299 (2009).
Hammer S.M.et al., "Treatment for adult HIV infection: 2006 recommendations of the International AIDS Society-USA panel.", JAMA, vol. 296, N°7, Aug. 2006, pp. 827-843.
Gazzard B. et al.,"British HIV Association (BHIVA) guidelines for the treatment of HIV-infected adults with antiretroviral therapy", HIV Med, vol. 7, N°8, Nov. 2006, pp. 487-503.
Domingo P. et al., "First line natiretroviral therapy with efavirenz or lopinavir/ritonavir plus two nucleoside analogues: the SUSKA study, a non-randomized comparison from the Vach cohort", Journal of Antimicrob.Chemother., vol. 61, N°6, Jun. 2008, pp. 1348-1358.
Lapadula G. et al, "Risk of early virological Failure of once-daily tenofovir-emtricitabine plus twice-daily nevirapine in antiretroviral therapy-naive HIV-infected patients", Clin.Infect. Dis., vol. 46, N°7, Apr. 2008, pp. 1127-1129.
Rey D. et al, "High rate of early virological failure with the once-daily tenofovir/mlamivudine/nevirapine combination in naive HIV-1-onfected patients-authors' repsonse", J. Antimicrob. Chemother, vol. 63, N°5, Feb. 2009, pp. 1080-1081.
Martin et al., "Relationship between adherence level, type of antiretroviral regimen and plasma HIV type I RNA Viral Load: a prospective cohort study", AIDS Research and Human retroviruses, Oct. 2008, vol. 24, N°10, pp. 1263-1268.
Parienti JJ et al, "Not all missed doses are the same: sustained NNRTI treatment interruptions predict HIV rebound at low-to-moderate adherence levels", PLoiS One, vol. 3, N°7, Jul. 2008.
Leon A et al, "Early virological failure in treatment-naive HIV-infected adults receiving didanosine and tenofovir plus efavirenz or neviraine", AIDS, vol. 19, N°2, Jan. 2005, pp. 213-215.
Arribas J.R., "the rise and fall of triple nucleoside reverse transcriptase inhibitor regimens", J. Antimicrob. Chemother, vol. 54, Jul. 2004, pp. 587-592.
Pinheiro et al., "A survey of the syntheses of active pharmaceutical ingredients for antiretroviral drug combinations critical to access in emerging nations.", Antiviral Research, vol. 79, N°3, Sep. 2008, pp. 143-165.
Project inform, Standard dosing Chart for anti-HIV drugs, Jan. 2006.
International Search Report dated Feb. 8, 2011, from the corresponding patent application.
International Search Report dated Feb. 8, 2011, from the patent application WO2011/061302.

* cited by examiner

*Primary Examiner* — Layla Bland
(74) *Attorney, Agent, or Firm* — Porzio, Bromberg & Newman, P.C.

(57) ABSTRACT

The present invention relates to a pharmaceutical composition for treating the human immunodeficiency virus (HIV) in a human being, comprising four active principles selected as being:
  a non-nucleoside inhibitor of reverse transcriptase (NNRTI) selected from nevirapine, efavirenz and etravirine;
  a nucleoside inhibitor of reverse transcriptase (NRTI) selected from lamivudine and emtricitabine; and
  two different nucleoside or nucleotide inhibitors of reverse transcriptase (NRTI) selected from didanosine, abacavir and tenofovir.

12 Claims, 6 Drawing Sheets

(EXAMPLE 4)

FTC: EMTRICITABINE; DDI: DIDANOSINE; TDF: TENOFOVIR; EFV: EFAVIRENZ.

QUADRUPLE THERAPY USEFUL FOR TREATING PERSONS AFFLICTED WITH THE HUMAN IMMUNODEFICIENCY VIRUS (HIV)

CROSS REFERENCE TO RELATED APPLICATION

This is a National Stage of International Application No. PCT/EP2010/067853, filed 19 Nov. 2010, which claims the benefit of Application No. 09176661.8, filed in Europe on 20 Nov. 2009, the disclosures of which Applications are incorporated by reference herein.

The present invention relates to a novel pharmaceutical composition useful for treating persons afflicted with the human immunodeficiency virus (HIV), which is responsible for the acquired immune deficiency syndrome (AIDS).

The human immunodeficiency virus (or HIV) is a retrovirus of the genus Lentivirus, i.e. a virus with a long period of incubation, which implies slow development of the disease.

Like all viruses, HIV is incapable of multiplying on its own. It must first invade a cell and take control of it. The target cells of HIV are those presenting CD4 receptors on their surface. Thus, CD4+ T lymphocytes, macrophages, dendritic cells and cerebral microglial cells can be infected with HIV.

When HIV infects a target cell, it takes control of it. Then the virus begins to make new copies of itself: this is the reproduction or replication phase. The virions thus produced infect other cells. In the absence of treatment, experts estimate that HIV can make up to 10 billion viral copies per day.

Two serotypes of HIV have been identified to date: HIV-1, which is present in most countries in the world, and HIV-2, which occurs mainly in West Africa.

It is commonly assumed that replication of the virus takes place in several main steps:
1—Fixation or attachment to a target cell
2—Fusion, penetration and decapsidation
3—Reverse transcription This step is specific to retroviruses: in fact, as the latter have RNA and not DNA for their genome, an operation of transcription, "converting" viral RNA to viral DNA, which alone can be integrated in the genome of the target cell, is necessary. This transcription is performed by the enzyme reverse transcriptase (RT).

4—Integration

The double-stranded DNA thus formed, closely associated with integrase and other viral and cellular protein components in a complex called preintegration complex, enters the cell nucleus. The DNA is then integrated randomly in the genome of the target cell, under the action of the enzyme integrase.

5—Formation of messenger RNA (mRNA)
6—Splicing of the mRNA thus obtained
7—Translation of the mRNA
8—Maturation
9—Assembly The structural proteins of the virus (matrix, capsid and nucleocapsid) are produced in the form of polyproteins. At the end of the maturation step, the various proteins are linked together and are transported to the membrane of the target cell, where they join the viral membrane glycoproteins. Viral RNAs join the viral proteins. The structural proteins assemble to form the capsid (protein envelope covering the DNA or RNA, the whole being denoted by nucleocapsid) and the matrix, which surrounds this assembly.

10—Budding

The capsid emerges from the infected cell.

11—Maturation of the viruses

A viral protease cleaves the bonds that join the various structural proteins (matrix, capsid and nucleocapsid). Following these cleavages, the virions (viral particles together with their outer protein envelope (capsid) and their RNA or DNA molecules inside) then become infectious and are ready to infect new cells.

Once seropositivity has been established, regular monitoring of the patient is put in place. Two main factors are usually monitored in order to track the development of the disease:

1—The level of CD4+ T lymphocytes

The level of CD4+ T lymphocytes is used for monitoring the progression of infection towards immune deficiency caused by HIV. The CD4+ T lymphocyte count corresponds to the number of T4 cells present in the blood. A normal level in humans is between 500 and 1500 CD4+T/mm$^3$ of blood. It has generally been assumed that:

up to 500 CD4+T/mm$^3$ of blood, the patient can live normally without requiring treatment;

starting from 350 CD4+T/mm$^3$ of blood, the offer of antiviral treatment is discussed, the expected result being control of the reproduction activity of the HIV, and, additionally, an at least partial rise in the CD4+T level;

below 200 CD4+T/mm$^3$ of blood, the patient is regarded as immunodepressed, running the risk of contracting diseases defining full-blown AIDS. Antiviral treatment with or without antibiotic prophylaxis is the only treatment capable of avoiding these complications.

2—Viral Load

The concentration of HIV viral particles in a volume of blood gives an objective estimate of the total number of virions freshly produced by the infected subject's body. Measurement is made according to standardized methods that vary little from one laboratory to another if it uses these validated methods. The result is given in log10 of the copy number/ml. The error in quantification (copy number of the virus) is such that a variation less than or equal to 0.5 is said to be not significant.

The difference between two measurements of viral load taken with a time interval allows the rate of reproduction of HIV to be evaluated and therefore the development of the infection. It is generally assumed that there is a link between the viral load and the level of immune deficiency, manifested by the disappearance of CD4+ T lymphocytes.

At the date of the present invention, the viral load is the best indicator of the development of the virus in the patient; based on current knowledge, it can also be suggested that a patient whose plasma viral load is below 50 copies/ml can be considered as a "non-transmitter of infection" by the mucosal route.

At the date of the present invention, there is no pharmaceutical composition for definitively eradicating HIV in a person who has contracted the virus, but certain compositions are able to suppress the HIV replication, said control being demonstrated by maintenance of a viral load constantly below 50 copies/ml of plasma. This control is able to stop progression of the disease to AIDS, and gives a life expectancy for the HIV carrier, correctly treated, near or equal to that of persons of the same age and of the same sex.

Since the beginning of the 1980s, numerous studies have led to the identification of a large number of antiretrovirals whose function is to interfere and block the various mechanisms required for replication of the HIV virus, by targeting more particularly one or other enzyme of HIV required for its replication or by affecting the physicochemical mechanisms governing entry of the virus into the target cell.

At the date of the present invention, antiretrovirals constitute the only medicinal products usefully employed against HIV. The first and principal objective of this therapy, notably in a patient who is naive of any treatment, is to keep the viral load below the detection threshold of 50 copies/ml of plasma for as long as possible, otherwise the antiviral therapy risks losing its efficacy over time, owing to the emergence of viruses that are resistant to the antiviral drugs administered (Hammer SM, Saag MS, Schechter M, et al., Treatment for adult HIV infection: 2006 recommendations of the International AIDS Society-USA panel. Top HIV Med (2006) 14:827-43)

The anti-HIV drugs are classified in four main classes of antiretrovirals, differing in their mode of action on the HIV virus and against its reproduction and/or its propagation in the carrier's body:

First there are the inhibitors of reverse transcriptase, which inhibit the conversion of viral RNA to proviral DNA, the first step in replication of the virus from the viral RNA. In this class, a distinction is made between:

nucleoside or nucleotide inhibitors of reverse transcriptase (NRTI); and non-nucleoside inhibitors (NNRTI)

The NRTIs correspond to the first class of antiretrovirals that were marketed. As examples of NRTI compounds, we may mention zidovudine (AZT, Retrovir®) and stavudine (d4T, Zerit®) (two thymidine analogs), didanosine (ddI, Videx®), abacavir (ABC, Ziagen®) and tenofovir (TDF, Viread®) (three adenosine analogs), and lamivudine (3TC, Epivir®) and emtricitabine (FTC, Emtriva®) (two cytosine analogs).

The NNRTIs are powerful selective inhibitors of HIV reverse transcriptase. As examples of NNRTI compounds we may mention nevirapine (NVP, Viramune®), etravirine (ETV, Intelence®), and efavirenz (EFV, Sustiva®). They are only active against HIV-1.

Next there are the inhibitors of HIV protease (PI) which act by inhibiting the action of the enzyme that directs the exact cutting of the viral proteins that are precursors of structures required for formation of the infectious HIV material, and notably the HIV virions, which are able to propagate in the organism and infect new permissive cells. Under the action of the inhibitors of HIV protease, pseudovirions are obtained, which are unable to infect new cells. As examples of PI compounds, we may mention, in their historical order of marketing, saquinavir (SQV, Invirase®), ritonavir (RTV, Norvir®), indinavir (IDV, Crixivan®), amprenavir (APV, Agenerase®), nelfinavir (NFV, Viracept®), atazanavir (ATZ, Reyataz®), fosamprenavir (FPV, Telzir®), tipranavir (TPV, Aptivus®), and darunavir (DRV, Prezista®).

Each of these PIs has the pharmacokinetic property of being eliminated rapidly from the patient's body by the cytochrome P450 pathway; partial blocking of this route of elimination by a product such as ritonavir, a powerful inhibitor of the cytochrome P450 functions, greatly prolongs the pharmaceutical lifetime of the PI prescribed. Ritonavir given at low doses "boosts" the anti-HIV protease administered to the patient at the same time, by increasing the levels in the blood, and prolonging its useful half-life in the organism.

There are also integrase inhibitors, which block the action of an enzyme of HIV whose elective function is to trim the ends of the HIV proviral DNA so as to make this DNA suitable to serve as a template for the transcription of the proviral DNA to HIV RNA. The integrase inhibitors make this enzyme instantly incapable of its function of DNA trimming, thus preventing reproduction of the viral genome in its target cell. As examples of integrase inhibitor compounds, we may mention raltegravir and elvitegravir (GS 9137).

Finally there are the fusion-lysis inhibitors, which are involved before the start of the biochemical cycle of HIV replication, by blocking the infectious progress of HIV at the level of certain proteins present on the surface of the virions, or by interfering with the binding capacities of these surface proteins with co-receptors that are present themselves on the surface of target cells of HIV. As examples of fusion-lysis inhibitor compounds, we may mention enfuvirtide (Fuzeon®) and maraviroc (Celsentri®).

Administered alone, most of the antiretrovirals have been shown to be only partially effective, and are generally incapable of sufficiently blocking the reproduction of HIV to obtain an optimum reduction in viral load or prevent it increasing again.

To overcome this deficiency, many combination therapies, and in particular triple therapies, have been developed over the years.

Triple therapy consists of the co-administration of three antiretrovirals, in the form of three different medicinal products administered separately, or in the form of a unit dosage form containing the three active principles.

Thanks to these combination therapies, and in particular the triple therapies used since 1996, mortality due to AIDS has been reduced significantly.

Based on their demonstrated efficacy, and their acceptability, the preferred antiretroviral combinations for starting anti-HIV therapy in patients without prior treatment have as their basis combinations of two NRTIs combined either with a PI boosted with ritonavir, or an NNRTI (Gazzard B. *British HIV Association (BHIVA) guidelines for treatment of HIV-infected adults with antiretroviral therapy* (2006). *HIV Med* (2006) 7:487-503).

Exceptionally, a third reverse transcriptase inhibitor is added to the combination consisting of a pair of nucleosides and an NNRTI to form a quadruple therapy, but the latter, as well as triple therapies combining three NRTIs, have not generally been validated.

However, many triple therapies available at the date of the present invention are characterized by viral breakthroughs, i.e. a viral load in the patient above 100 copies/ml of plasma measured during two close consecutive dosages; the level of "viral breakthroughs" increasing with the years of uninterrupted administration. In these cases, the level of breakthroughs rises to 10% or more of patients treated after just 48 weeks of treatment, and can exceed 20% or even 30% after 3 or 4 years of uninterrupted treatments. These breakthroughs are a sign of suboptimal antiviral combinations, and put forward many situations in which there may be a selection of HIV viruses bearing mutations of at least partial resistance to the medicinal components of the combination (*First-line antiretroviral therapy with efavirenz or lopinavir/ritonavir plus two nucleoside analogues: the SUSKA study, a non-randomized comparison from the VACH cohort*, Pere Domingo et al., *Journal of Antimicrobial Chemotherapy* (2008) 61, 1348-1358). This is the case in particular with most triple therapies combining only three reverse transcriptase inhibitor components and triple therapies combining two reverse transcriptase inhibitor components with nevirapine. (*Risk of Early Virological Failure of Once-Daily Tenofovir-Emtricitabine plus Twice-Daily Nevirapine in Antiretroviral Therapy-Naive HIV-Infected Patients*, Giuseppe Lapadula, Silvia Costarelli, Eugenia Quiros-Roldan, et al., *Clinical Infectious Diseases* 2008, 46:1127-1129; and *High rate of early viro-*

*logical failure with the once-daily tenofovir/lamivudine/nevirapine combination in naive HIV-1-infected patients—authors' response*, D. Rey, B. Hoen, P. Chavanet, et al., *J. Antimicrob. Chemother* 2009; 63: 1080-1081).

Furthermore, many undesirable side effects are associated with the use of these drugs, including lactic acidosis, characterized by deep, rapid breathing, somnolence, nausea, vomiting and/or stomach pains; sensations of vertigo; sleep disorders; difficulty concentrating; abnormal dreams; skin rashes; various inflammations or infections; and/or bone disorders, etc.

At the date of the present invention, two triple therapies (Trizivir®, a medicinal product marketed by the GlaxoSmithKline pharmaceutical laboratory and Atripla®, a medicinal product marketed by the Gilead pharmaceutical laboratory) allow daily administration of the treatment seven days a week as a unit dosage form. Trizivir® is in the form of a single film-coated tablet comprising:

150 mg of lamivudine;
300 mg of zidovudine; and
300 mg of abacavir base (351 mg of abacavir sulfate).

Atripla® is in the form of a single film-coated tablet comprising:

600 mg of efavirenz;
200 mg of emtricitabine; and
245 mg of tenofovir disoproxil fumarate (expressed as tenofovir disoproxil).

This second pharmaceutical composition, which is among the most effective triple therapies currently marketed, nevertheless requires daily administration seven days a week, which certainly does not promote best patient compliance with the treatment.

Neither Atripla®, nor Trizivir® has been able to reduce the undesirable effects mentioned above.

Moreover, according to the Guidelines issued by the Food and Drug Administration (FDA) in 2008 (FDA Guidelines 2008), efavirenz cannot be used in pregnant women. Thus, Atripla®, which contains efavirenz, cannot, by extension, be used in pregnant women, which obviously is a serious drawback.

Finally, the need for daily administration seven days a week makes these therapies onerous and restricting for the patients, and tends to increase the intensity of the side effects that they experience. Because of this, patients often do not strictly observe the recommendations in terms of administration of the therapy.

In 2007, an isolated study attempted to demonstrate that it was possible to reduce the weekly administration of various existing triple therapies to five days (*Pilot Study of a Novel Short-Cycle Antiretroviral Treatment Interruption Strategy: 48-Week Results of the Five-Days-On, Two-Days-Off (FOTO) Study*, Calvin J. Cohen, M D, Amy E. Colson, Alexander G. Sheble-Hall, et al., *HIV Clin Trials* 2007; 8(1):19-23). In this study, conducted on thirty patients whose HIV virus is controlled durably by various uninterrupted triple therapies, the weekly treatment regimen was reduced to five days per week (with two days off). At the 24th and 48th week of this treatment, the virus was still under control in 26 out of 29 patients (89.6%). However, even the authors admit that the benefits seen in the "FOTO" study are still very uncertain and these dosage regimens should not be used before these results are confirmed in a larger study. Moreover, this document gives no indication regarding the possibility of a possible further reduction in the number of weekly administrations of the existing triple therapies.

However, these studies are still isolated and, at the date of the present invention, most specialists agree in considering that a decrease in the number of weekly administrations of existing triple therapies would not fail to increase the number of viral breakthroughs in the patients treated. Thus, a decrease in the number of weekly administrations of existing triple therapies is generally associated with certain therapeutic failure. As an example, Professor Delfraissy regards noncompliance with the treatment as the main cause of therapeutic failure ("*Therapeutic management of persons infected with HIV—Report* 2004—*Under the supervision of Professor Jean-Francois Delfraissy*, 2004, Éditions Flammarion, p. 48-49).

Moreover, a study published after the "FOTO" study (*Relationship between Adherence Level, Type of the Antiretroviral Regimen, and Plasma HIV Type 1 RNA Viral Load: A Prospective Cohort Study*, M. Martin, E. Del Cacho, C. Codina, et al., *AIDS Research and Human Retroviruses*, October 2008, 24(10): 1263-1268. doi:10.1089/aid.2008.0141) well summarizes the predominant prejudice according to which reducing the amount of antivirals in a patient must lead to a resumption of HIV replication, in inverse proportion to the pressure exerted daily by the triple therapy in question. Thus, compared with patients observing the prescribed treatment at more than 90%, this study notes a risk of viral breakthrough:

9 times greater in patients only complying with the treatment at 80 to 89.9%, or, for triple therapy assuming daily administration seven days a week, for patients taking their treatment about six days out of seven;

45.6 times greater in patients only complying with the treatment at 70 to 79.9%, or, for triple therapy assuming daily administration seven days a week, for patients taking their treatment about five to six days out of seven; and 77.3 times greater in patients only complying with the treatment at less than 70%, or, for triple therapy assuming daily administration seven days a week, for patients taking their treatment less than five days out of seven.

Moreover, another study also published after the "FOTO" study (*Not all missed doses are the same: sustained NNRTI treatment interruptions predict HIV rebound at low-to-moderate adherence levels*, Parienti J J, Das-Douglas M, Massari V, Guzman D, Deeks S G, Verdon R, Bangsberg D. R., PLoS One, Jul. 30, 2008; 3(7):e2783) teaches that any interruption of treatment of more than 2 days increases the risks of virological "rebound", i.e. the risks of a resumption of HIV replication.

Finally, the cost per patient and per year of the combination therapies available at the date of the present invention is still excessively high. For example, Atripla® is sold in France in the form of a bottle containing 30 tablets (i.e. a month of treatment) at the price of 834.30€, or an annual cost per patient of about 10,000€. Now, although the current treatments can greatly limit the development of the HIV virus in patients, in no case are they able to eradicate it. The cost of treating persons with HIV can therefore reach very substantial sums, which are likely to increase considerably in future.

Thus, it remains more than ever necessary to develop alternative combination therapies that can limit the number of administrations of the treatment to the patient to ensure better patient compliance, limit the undesirable effects associated with this treatment and lower the costs associated with the latter, while maintaining therapeutic efficacy at least comparable to that of the existing combination therapies, and in particular Atripla®.

Other combination therapies have been tested since Atripla® was first marketed. As an example, we may mention the study reported by the company Boehringer Ingelheim Pharmaceuticals in *Biotech Finances* dated Jul. 20, 2009.

This publication gives the results of a comparative study on two triple therapies: one consisting of administering nevirapine combined with tenofovir and emtricitabine, and the other consisting of administering atazanavir/ritonavir combined with tenofovir and emtricitabine. Each of these combinations was administered once daily. Moreover, this study emphasized that an increase in viral load was observed after 48 weeks of treatment in nearly 35% of the patients treated.

Ferrer E, Gatell J M, Sanchez P, Domingo P et al. reported, in AIDS Res Hum Retroviruses, 2008-07; 24(7):931-4, the assessment of a quadruple therapy combining zidovudine, lamivudine, abacavir and tenofovir, i.e. four NRTIs, at standard doses during an uncontrolled prospective pilot trial of 96 weeks in adults with HIV who had not had any prior treatment. Only 34 out of the 39 patients treated (87%) reached a viral load less than or equal to 50 copies/ml at the 96th week, which represents 13% of virological failures. This work makes no mention of a quadruple therapy combining 3 NRTIs with one NNRTI, nor any decrease in the number of weekly administrations of said quadruple therapy thus evaluated.

A novel pharmaceutical composition for treating HIV has now been found, unexpectedly, which allows the number of administrations to the patient to be reduced, while maintaining efficacy at least comparable to that of the existing combination therapies, and in particular Atripla®.

The present invention therefore relates to a pharmaceutical composition for treating the human immunodeficiency virus (HIV) in a human being, comprising four active principles selected as being:
- a non-nucleoside inhibitor of reverse transcriptase (NNRTI) selected from nevirapine, efavirenz and etravirine;
- a nucleoside inhibitor of reverse transcriptase (NRTI) selected from lamivudine and emtricitabine; and
- two different nucleoside or nucleotide inhibitors of reverse transcriptase (NRTI) selected from didanosine, abacavir and tenofovir.

The pharmaceutical composition according to the invention makes it possible not only to decrease the number of administrations to the patient, while maintaining efficacy at least comparable to that of the existing combination therapies, and in particular Atripla®. Moreover, the composition according to the invention can also be administered to pregnant women, which makes it possible, among other things, to carry out the treatment starting from the first months of pregnancy, even unexpected.

These results are all the more unexpected because didanosine is an antiretroviral that is known to have a low capacity for preventing, on its own, the replication of HIV (low "intrinsic antiviral potency"). The authors Jemsek J., Hutcherson P., and Harper E. report, moreover, in their article "*Poor virologic responses and early emergence of resistance in treatment naive, HIV-infected patients receiving a once daily triple nucleoside regimen of didanosine, lamivudine, and tenofovir*" (DF. 11th Conference on Retroviruses and Opportunistic Infections, San Francisco, Feb. 8-11, 2004, Abstract 51) an early virological failure rate of 91% when using the triple therapy combining didanosine, tenofovir and lamivudine.

Moreover, the studies reported by Agathe Leon, Esteban Martinez, Josep Mallolas, et al., *Early virological failure in treatment-naïve HIV-infected adults receiving didanosine and tenofovir plus efavirenz or Nevirapine* (AIDS 2005, 19:209-215); and Jose R. Arribas, *The rise and fall of triple nucleoside reverse transcriptase inhibitor regimens* (Journal of Antimicrobial Chemotherapy (2004) 54, 587-592) showed a very high rate of early virological failure (50% or more) when using triple therapies combining tenofovir and didanosine with an NNRTI such as efavirenz or nevirapine.

In the context of the present invention:
HIV denotes exclusively HIV-1;
"pharmaceutically acceptable salt" of an active principle means any salt of addition of said active principle with a mineral or organic acid by the action of said acid in an organic or aqueous solvent such as an alcohol, a ketone, an ether or a chlorinated solvent, and which is pharmaceutically acceptable;
"pharmaceutically acceptable derivative" of an active principle means any "prodrug" or "metabolite" of said active principle, as well as a pharmaceutically acceptable salt thereof;
"prodrug" of an active principle means any compound whose biotransformation in the body leads to said active principle;
"metabolite" of an active principle means any intermediate resulting from the transformation of said active principle in the body during a metabolic process;
"daily administration" means administration once daily or administration once every 24 hours;
"continuous schedule" means the continuous therapeutic treatment of a patient, comprising the successive administration of one or more therapeutic compositions (including combination therapies, whether or not according to the invention), identical or different, each with its own regimen of therapeutic administration (number of daily administrations and number of days of administration in a given period, a week for example) and this without limit and not sequenced or spaced out over time, i.e. without interruption of treatment;
nevirapine (or NVP) denotes 11-cyclopropyl-5,11-dihydro-4-methyl-6H-dipyrido[3,2-b:2',3'-f][1,4]diazepin-6-one, and pharmaceutically acceptable salts or derivatives thereof;
efavirenz (or EFV) denotes (S)-6-chloro-4-(cyclopropylethynyl)-1,4-dihydro-4-(trifluoromethyl)-2H-3,1-benzoxazin-2-one, and pharmaceutically acceptable salts or derivatives thereof;
etravirine (or ETV) denotes 4-({6-amino-5-bromo-2-[(4-cyanophenyl)amino]pyrimidin-4-yl}oxy)-3,5-dimethylbenzonitrile, and pharmaceutically acceptable salts or derivatives thereof;
lamivudine (or 3TC) denotes (2R,5S)-(-)-4-amino-1-[2-(hydroxymethyl)-1,3-oxathiolan-5-yl]-1H-pyrimidin-2-one, and pharmaceutically acceptable salts or derivatives thereof;
emtricitabine (or FTC) denotes L-2',3'-dideoxy-5-fluoro-3'-thiacytidine, and pharmaceutically acceptable salts or derivatives thereof;
didanosine (or DDI) denotes L-2',3'-dideoxyinosine, and pharmaceutically acceptable salts or derivatives thereof;
abacavir (or ABC) denotes [(1S,4R)-4-[2-amino-6-(cyclopropylamino)-9H-purin-9-yl]cyclopent-2-enyl]methanol, and pharmaceutically acceptable salts or derivatives thereof, including abacavir sulfate; and
tenofovir (or TDF) denotes L (R)-9-(2-phosphonylmethoxypropyl)adenine, and pharmaceutically acceptable salts or derivatives thereof, including tenofovir disoproxil or tenofovir disoproxil fumarate.

Preferably, the present invention relates to a pharmaceutical composition as defined above, in which the following features are selected, alone or in combination:
the NNRTI is selected as being nevirapine;
the "first" NRTI is selected as being emtricitabine;

the other two NRTIs are selected as being tenofovir and didanosine.

Quite preferably, the present invention relates to a pharmaceutical composition comprising, as active principles, nevirapine, emtricitabine, tenofovir and didanosine.

As other examples of pharmaceutical compositions according to the present invention, we may notably mention the pharmaceutical compositions comprising:

nevirapine, emtricitabine, abacavir, and didanosine;
nevirapine, lamivudine, abacavir and didanosine;
nevirapine, lamivudine, tenofovir and didanosine;
efavirenz, emtricitabine, abacavir, and didanosine;
efavirenz, emtricitabine, tenofovir and didanosine;
efavirenz, lamivudine, abacavir and didanosine;
efavirenz, lamivudine, tenofovir and didanosine;
etravirine, emtricitabine abacavir, and didanosine;
etravirine, emtricitabine, tenofovir and didanosine;
etravirine, lamivudine, abacavir and didanosine; and
etravirine, lamivudine, tenofovir and didanosine.

The pharmaceutical composition according to the present invention contains the active principles in a sufficient amount to ensure the desired therapeutic effect, i.e. treatment of HIV while maintaining, in the patient treated, a viral load below 50 copies/ml, preferably less than or equal to 20 copies/ml.

If necessary, the pharmaceutical composition according to the present invention also makes it possible to maintain or restore the level of CD4+ T lymphocytes at a level preferably above the patient's CD4+T/mm$^3$ level before the antiviral treatment with the composition of the invention.

Preferably, the following amounts of antiretrovirals are used for preparing the pharmaceutical composition according to the invention:

from 100 to 300 mg of emtricitabine, preferably 200 mg of emtricitabine;
from 200 to 400 mg of lamivudine, preferably 300 mg of lamivudine;
from 500 to 700 mg of abacavir, preferably 600 mg of abacavir;
from 100 to 300 mg of tenofovir, preferably 245 mg of tenofovir;
from 150 to 350 mg of didanosine, preferably 250 mg of didanosine;
from 300 to 500 mg of nevirapine, preferably 400 mg of nevirapine;
from 300 to 500 mg of etravirine, preferably 400 mg of etravirine;
from 100 to 700 mg of efavirenz, preferably 200, 400 or 600 mg of efavirenz.

The pharmaceutical composition according to the present invention can be formulated in any pharmaceutical form necessary for its administration. In particular, in the case of administration by the oral route, the compositions according to the present invention can be formulated in the form of coated or uncoated, effervescent, soluble, orodispersible, enteric or modified-release tablets; sugar-coated tablets; hard capsules; soft capsules; granules; granulate; pills; pastilles. In the case of systemic administration, the composition according to the invention can be formulated in the form of sterile lyophilized powder for injection. The pharmaceutical compositions according to the present invention can therefore comprise, in addition to the active principles, any pharmaceutically acceptable excipient known by a person skilled in the art and which is necessary for preparing the pharmaceutical composition in the desired form.

Certain pharmaceutical compositions according to the present invention can be administered to any patient infected with HIV, including pregnant women. Thus, the present invention also relates to a pharmaceutical composition as defined above and in which the NNRTI is selected from nevirapine and etravirine, for treating the human immunodeficiency virus (HIV) in pregnant women.

The pharmaceutical composition according to the present invention makes it possible to reduce the number of administrations to the patient while maintaining efficacy at least comparable to that of the existing combination therapies, and in particular Atripla®. Thus, the present invention also relates to a pharmaceutical composition as defined above for daily administration one to seven days per week, preferably one to six days per week, more preferably one to four days per week, quite preferably two to four days per week, to a human being infected with HIV.

The pharmaceutical composition according to the invention can be administered at any time of day, before, during or after meals, without any effect on the efficacy of the treatment.

The pharmaceutical composition according to the invention can be administered according to a continuous schedule.

The present invention further relates to the use of a pharmaceutical composition as defined above for preparing a medicinal product intended for treating HIV in human beings.

The present invention further relates to the use of a pharmaceutical composition as defined above and in which the NNRTI is selected from nevirapine and etravirine for preparing a medicinal product intended for treating HIV in pregnant women.

The present invention further relates to the use of a pharmaceutical composition as defined above for preparing a medicinal product intended for treating HIV in a human being, said medicinal product being administered daily one to seven days per week, preferably one to six days per week, more preferably one to four days per week, quite preferably two to four days per week, to said human being, and administration may or may not be carried out according to a continuous schedule.

The present invention also relates to a method of treating HIV in a human being infected with this virus by administering a pharmaceutical composition as defined above.

The present invention also relates to a method of treating HIV in pregnant women infected with this virus by administering a pharmaceutical composition as defined above and in which the NNRTI is selected from nevirapine and etravirine.

The present invention also relates to a method of treating HIV in a human being infected with this virus by daily administration, one to seven days per week, preferably one to six days per week, more preferably one to four days per week, quite preferably two to four days per week, of a pharmaceutical composition as defined above, and administration may or may not be carried out according to a continuous schedule.

The four active principles constituting the novel combination therapy according to the invention can be administered in the form of a unit pharmaceutical composition comprising the four active principles permitting administration of said composition to the patient in a single dose.

However, separate administration of one or more of the active principles constituting the pharmaceutical composition according to the invention can also be envisaged. Thus, the present invention also relates to a pharmaceutical product containing:

a non-nucleoside inhibitor of reverse transcriptase (NNRTI) as defined above; and
three nucleoside or nucleotide inhibitors of reverse transcriptase (NRTI) as defined above;

as a combination product (or pharmaceutical kit) for simultaneous, separated or spread over time administration for treating of HIV in a human being.

For example, the pharmaceutical product according to the present invention can be in the form of:
- a unit dosage form containing an NRTI as defined above and a unit dosage form containing the other two NRTIs and an NNRTI as defined above; or
- a unit dosage form containing an NNRTI as defined above and a unit dosage form containing the three NRTIs as defined above; or
- a unit dosage form containing an NRTI and an NNRTI as defined above and a unit dosage form containing the other two NRTIs as defined above;
- a unit dosage form containing an NRTI and an NNRTI as defined above and the other two unit dosage forms each containing an NRTI as defined above; or
- a unit dosage form containing two NRTIs as defined above, a unit dosage form containing an NNRTI as defined above and a unit dosage form containing an NRTI as defined above;
- four unit dosage forms containing respectively four active principles according to the invention, as defined above.

In the context of the present invention, the unit dosage form containing nevirapine and didanosine constitutes a specific, preferred pharmaceutical entity.

Thus, as preferable examples, we may mention the pharmaceutical product in the form of:
- a unit dosage form containing nevirapine and didanosine, and a unit dosage form containing abacavir and lamivudine (marketed under the name Kivexa®);
- a unit dosage form containing nevirapine and didanosine, a unit dosage form containing abacavir, and a unit dosage form containing lamivudine;
- a unit dosage form containing nevirapine and didanosine, and a unit dosage form containing emtricitabine and tenofovir (marketed under the name Truvada®);
- a unit dosage form containing nevirapine and didanosine, and a unit dosage form containing abacavir and emtricitabine;
- a unit dosage form containing nevirapine and didanosine, a unit dosage form containing abacavir, and a unit dosage form containing emtricitabine;
- a unit dosage form containing nevirapine and didanosine, and a unit dosage form containing abacavir and tenofovir; or
- a unit dosage form containing nevirapine and didanosine, a unit dosage form containing abacavir, and a unit dosage form containing tenofovir.

The pharmaceutical product according to the invention can of course be administered according to one of the administration regimens defined above. Thus, the present invention also relates to a pharmaceutical product containing:
- a non-nucleoside inhibitor of reverse transcriptase (NNRTI) as defined above; and
- three nucleoside or nucleotide inhibitors of reverse transcriptase (NRTI) as defined above;

as a combination product (or pharmaceutical kit) for simultaneous, separated or spread over time administration one to seven days per week, preferably one to six days per week, more preferably one to four days per week, quite preferably two to four days per week, for treating HIV in a human being.

Figure 1:
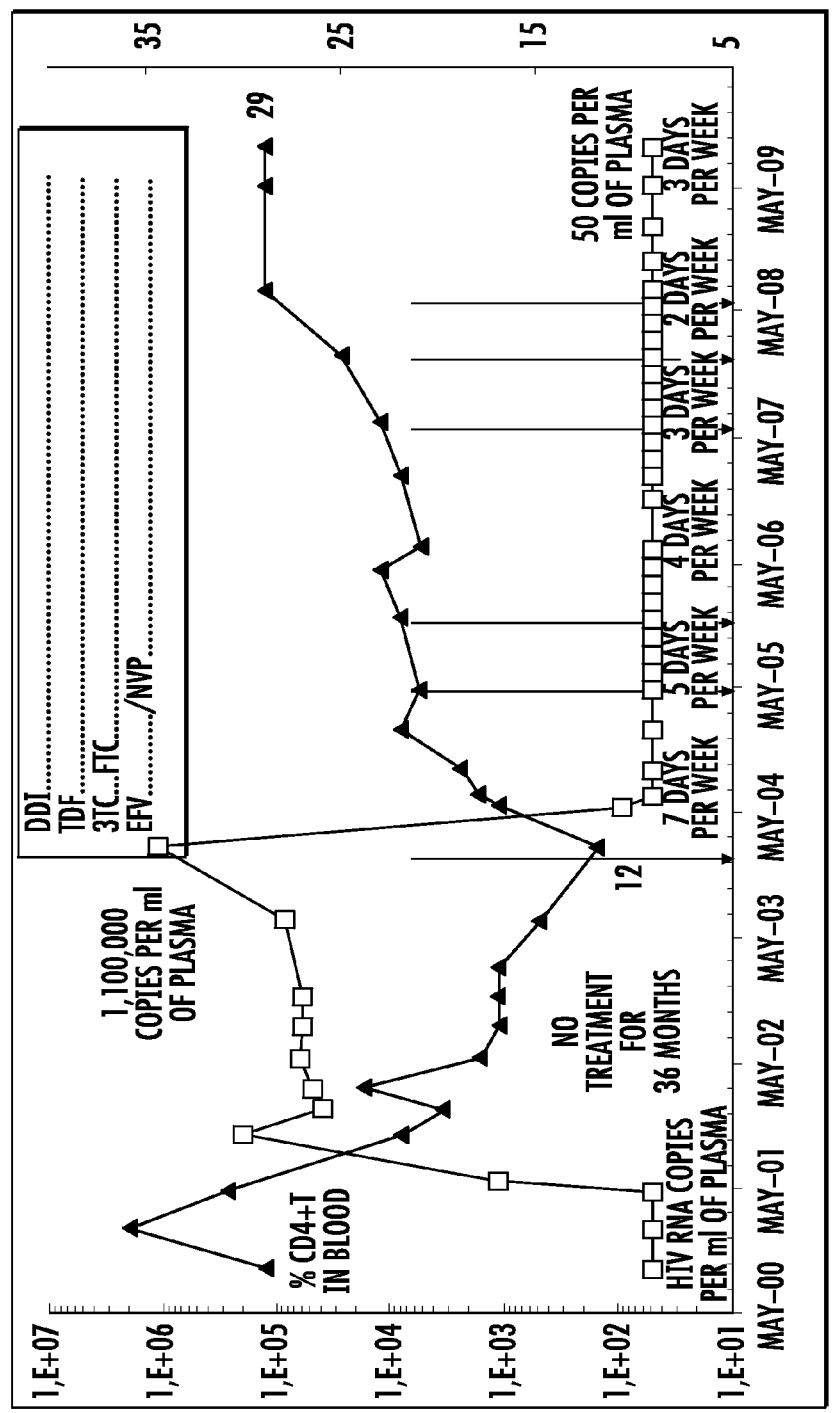
FIG. 1 is a graph showing the plasma viral load and the CD4+ T level in the blood measured in a patient infected with HIV, untreated during 36 months and then, treated during 6 years with a protocol of consecutive quadruple therapies.

The present invention is illustrated non-exhaustively by the following examples.

In the following examples (examples 1 to 8), the daily doses of active principle used for treating the patients correspond, unless stated otherwise, to the following doses:
- 200 mg of emtricitabine;
- 300 mg of lamivudine;
- 600 mg of abacavir;
- 245 mg of tenofovir;
- 250 mg of didanosine;
- 400 mg of nevirapine;
- 400 mg of etravirine;
- 600 mg of efavirenz.

Example 1

A patient infected with HIV, untreated for 36 months, was treated according to the following protocol:
- treatment with a quadruple therapy combining efavirenz (EFV), lamivudine (3TC), and tenofovir (TDF) and didanosine (DDI), administered daily 7 days per week;
- then treatment with a quadruple therapy combining efavirenz (EFV), emtricitabine (FTC), and tenofovir (TDF) and didanosine (DDI), administered daily 7 days per week;
- and finally treatment with a quadruple therapy combining nevirapine (NVP), emtricitabine (FTC), and tenofovir (TDF) and didanosine (DDI), administered daily 7 days per week, then 5 days per week, then 4 days per week, then 3 days per week, then 2 days per week.

The plasma viral load and the CD4+T level in the blood were measured during this treatment.

The results are presented in FIG. 1.

Throughout the treatment period, the patient's plasma viral load remained less than or equal to 50 copies/ml of plasma without any viral breakthrough being observed. Moreover, a rise in the CD4+T level in the blood was also observed.

Example 2

A patient infected with HIV was treated with a quadruple therapy combining nevirapine (NVP), emtricitabine (FTC), and tenofovir (TDF) and didanosine (DDI), administered daily 7 days per week, then 5 days per week, then 4 days per week, then 3 days per week.

The plasma viral load and the CD4+T level in the blood were measured during this treatment.

Figure 2:
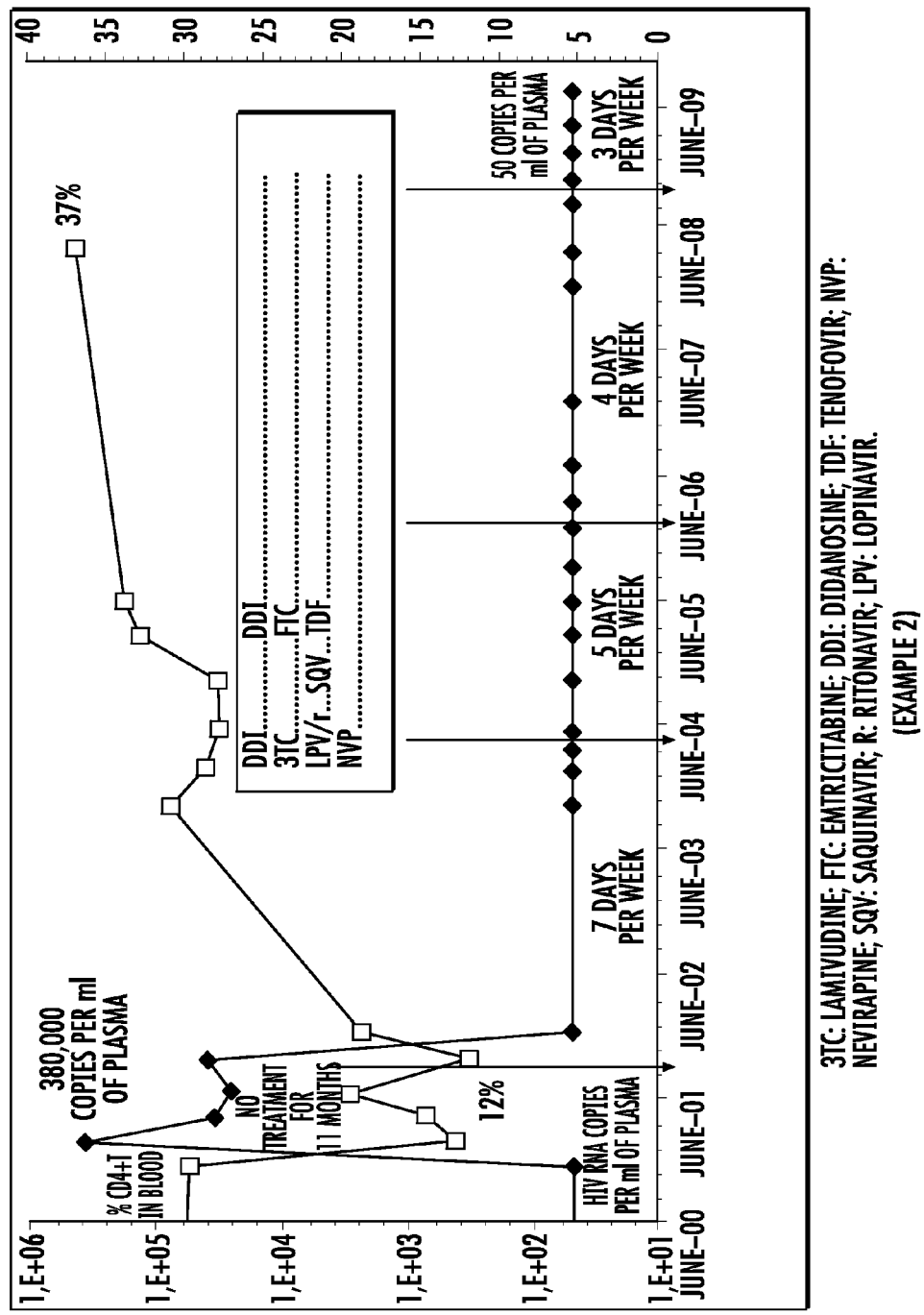
FIG. 2 is a graph showing the plasma viral load and the CD4+ T level in the blood measured in a patient infected with HIV, untreated during 11 months and then, treated during 8 years with a quadruple therapy combining nevirapine (NVP), emtricitabine (FTC), tenofovir (TDF) and didanosine (DDI).

The results are presented in FIG. 2.

Throughout the treatment period, the patient's plasma viral load remained less than or equal to 50 copies/ml of plasma without any viral breakthrough being observed. Moreover, a rise in the CD4+T level in the blood was also observed.

Example 3

A patient infected with HIV was treated with a quadruple therapy combining nevirapine (NVP), emtricitabine (FTC), and tenofovir (TDF) and didanosine (DDI), administered daily 7 days per week, then 5 days per week, then 4 days per week, then 3 days per week.

The plasma viral load and the CD4+T level in the blood were measured during this treatment.

Figure 3:
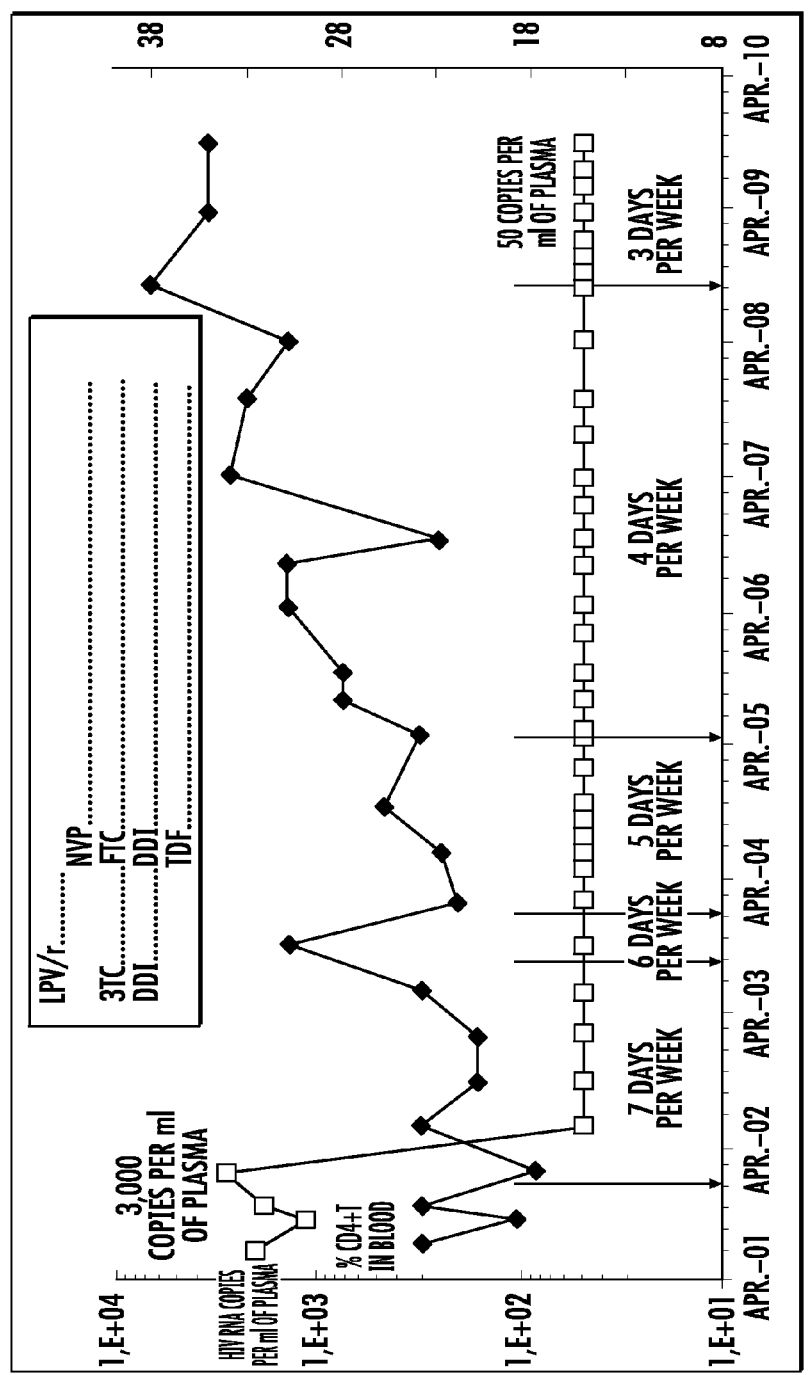
FIG. 3 is a graph showing the plasma viral load and the CD4+ T level in the blood measured in a patient infected with HIV, treated with a quadruple therapy combining nevirapine (NVP), emtricitabine (FTC), tenofovir (TDF) and didanosine (DDI).

The results are presented in FIG. 3.

Throughout the treatment period, the patient's plasma viral load remained less than or equal to 50 copies/ml of plasma without any viral breakthrough being observed. Moreover, a rise in the CD4+T level in the blood was also observed.

Example 4

A patient infected with HIV was treated according to the following protocol:
 treatment with a quadruple therapy combining efavirenz (EFV) 600 mg, emtricitabine (FTC), and tenofovir (TDF) and didanosine (DDI), administered daily 7 days per week;
 then treatment with a quadruple therapy combining efavirenz (EFV) 400 mg, emtricitabine (FTC), and tenofovir (TDF) and didanosine (DDI), administered daily 5 days per week, then 4 days per week, then 3 days per week, then 2 days per week.

The plasma viral load and the CD4+T level in the blood were measured during this treatment.

Figure 4:
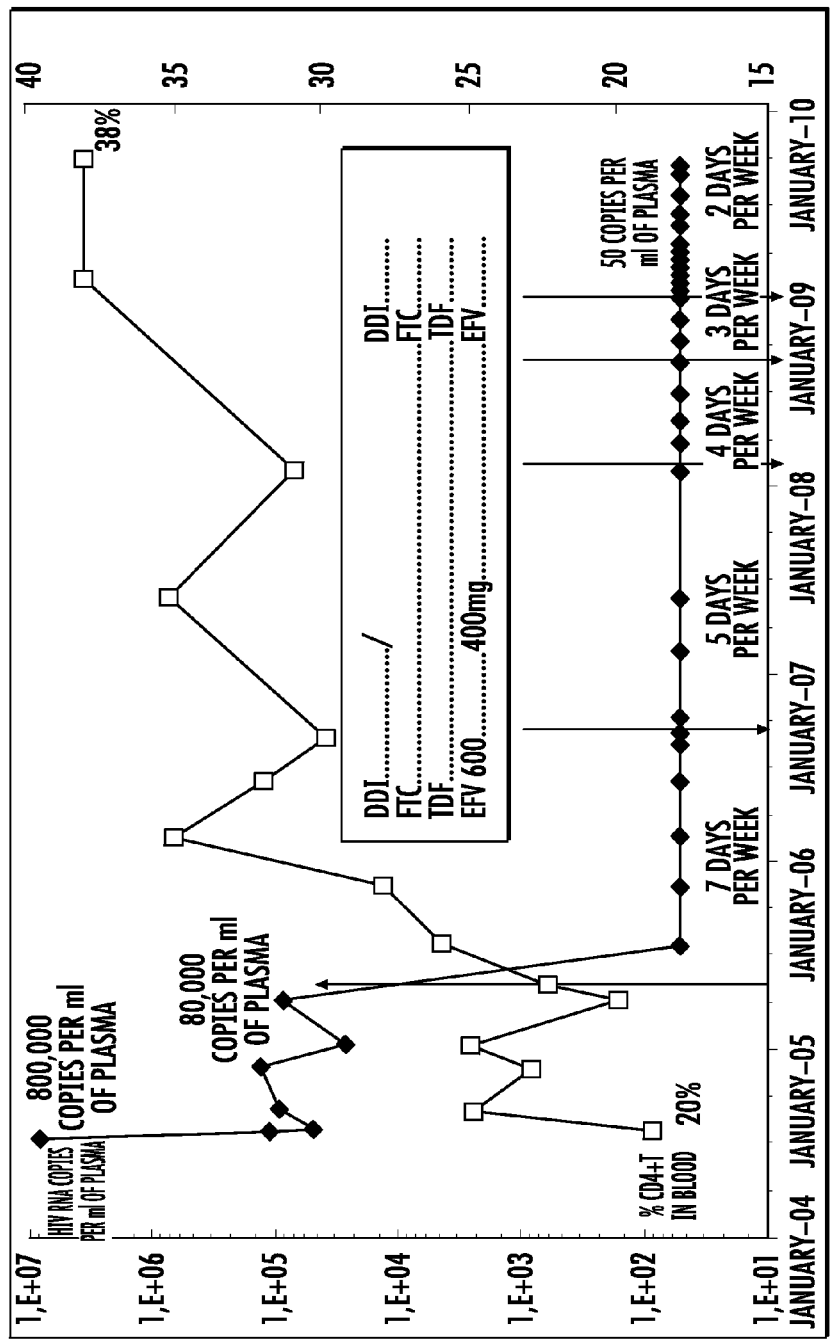
FIG. 4 is a graph showing the plasma viral load and the CD4+ T level in the blood measured in a patient infected with HIV, treated with a quadruple therapy combining efavirenz (EFV), emtricitabine (FTC), tenofovir (TDF) and didanosine (DDI).

The results are presented in FIG. 4.

Throughout the treatment period, the patient's plasma viral load remained less than or equal to 50 copies/ml of plasma without any viral breakthrough being observed. Moreover, a rise in the CD4+T level in the blood was also observed.

Example 5

A patient infected with HIV, untreated for 24 months, was treated according to the following protocol:
 treatment with a quadruple therapy combining efavirenz (EFV), emtricitabine (FTC), and tenofovir (TDF) and didanosine (DDI), administered daily 7 days per week, then 5 days per week;
 then treatment with a triple therapy;
 and finally treatment with a quadruple therapy combining etravirine (ETV), emtricitabine (FTC), and tenofovir (TDF) and didanosine (DDI), administered daily 3 days per week.

The plasma viral load and the CD4+T level in the blood were measured during this treatment.

Figure 5:
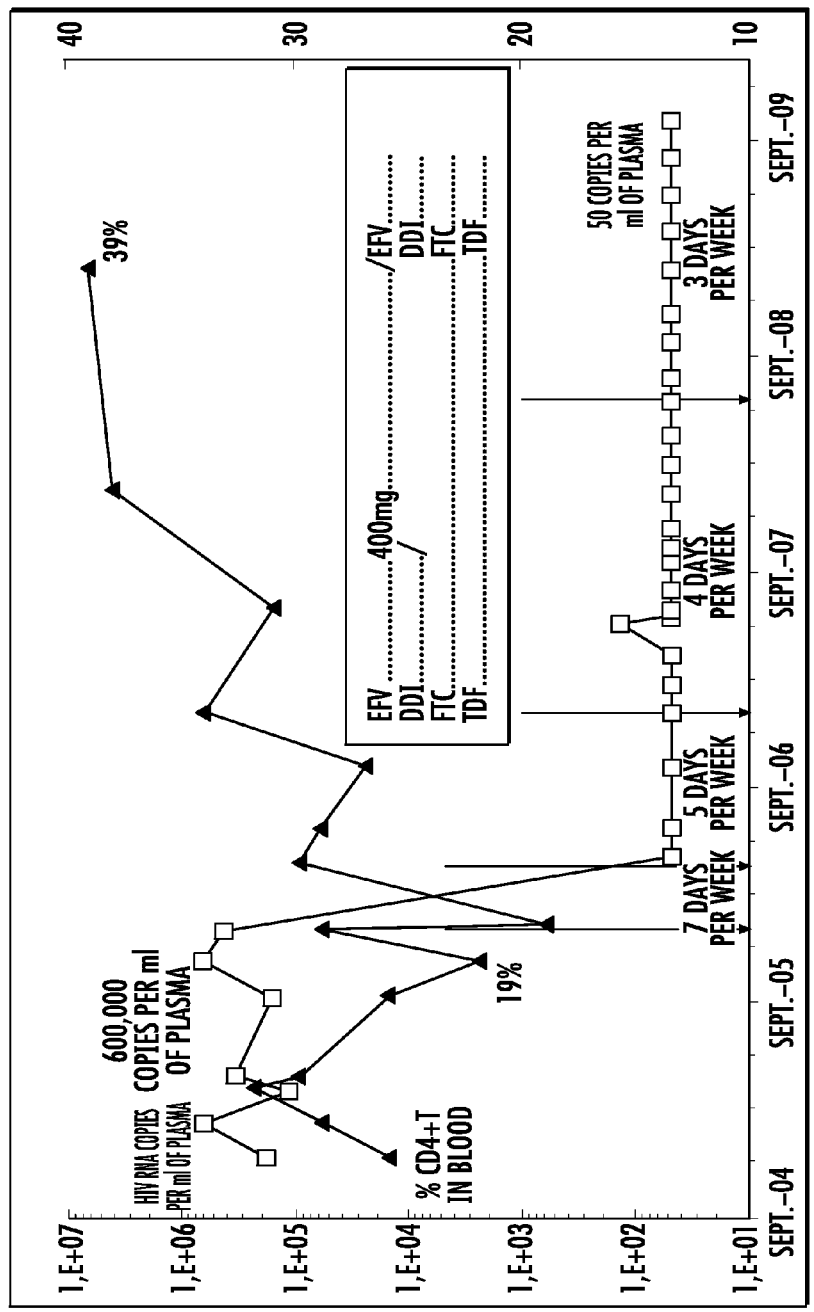
FIG. 5 is a graph showing the plasma viral load and the CD4+ T level in the blood measured in a patient infected with HIV, untreated for 24 months, and then treated with a protocol comprising both tritherapy and quadruple therapy combining efavirenz (EFV) or etravirine (ETV), emtricitabine (FTC), tenofovir (TDF) and didanosine (DDI).

The results are presented in FIG. 5.

Throughout the treatment period, the patient's plasma viral load remained less than or equal to 50 copies/ml of plasma without any viral breakthrough being observed. Moreover, a rise in the CD4+T level in the blood was also observed.

Example 6

A patient infected with HIV, untreated for 24 months, was treated according to the following protocol:
 treatment with a quadruple therapy combining efavirenz (EFV) 400 mg, lamivudine (3TC), and tenofovir (TDF) and didanosine (DDI), administered 7 daily days per week, then 5 days per week;
 then treatment with a triple therapy;
 and finally treatment with a quadruple therapy combining efavirenz (EFV) 200 mg, emtricitabine (FTC), and tenofovir (TDF) and didanosine (DDI), administered daily 3 days per week, then 2 days per week.

The plasma viral load and the CD4+T level in the blood were measured during this treatment.

Figure 6:
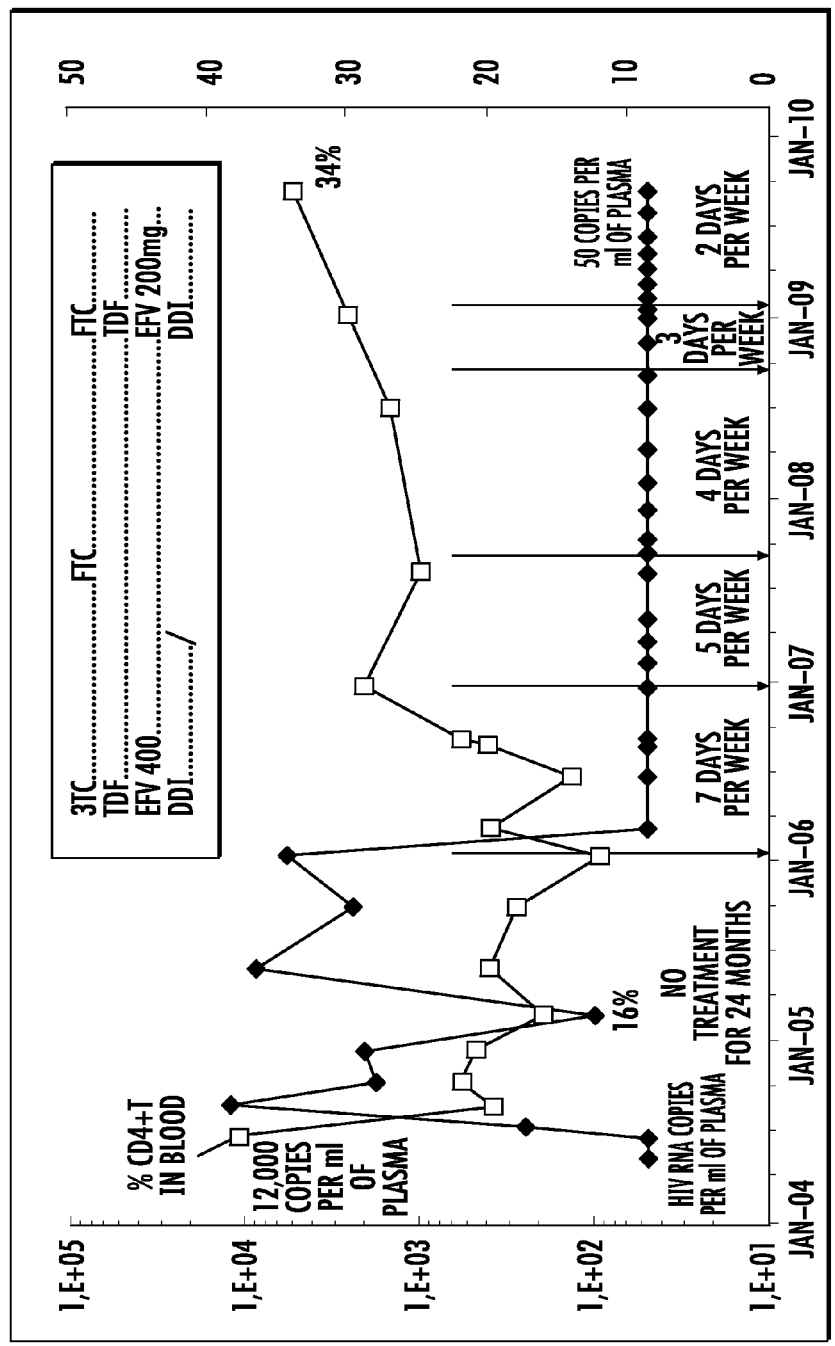
FIG. 6 is a graph showing the plasma viral load and the CD4+ T level in the blood measured in a patient infected with HIV, untreated for 24 months, and then treated with a protocol comprising both tritherapy and quadruple therapy combining efavirenz (EFV), lamivudine (3TC) or emtricitabine (FTC), tenofovir (TDF) and didanosine (DDI).

The results are presented in FIG. 6.

Throughout the treatment period, the patient's plasma viral load remained less than or equal to 50 copies/ml of plasma without any viral breakthrough being observed. Moreover, a rise in the CD4+T level in the blood was also observed.

Example 7

The number of "HIV blips" during treatment, i.e. transient appearances of HIV in the plasma above 50 copies per ml of plasma in the patients treated, was measured in patients being treated with Atripla® in comparison with patients treated with the quadruple therapies according to the invention.

The results obtained are presented in the following table.

| Treatment | Efavirenz + 2 NRTIs (Atripla ® and others) (Number of "blips"/ number of patients) | Nevirapine + 3 NRTIs (Number of "blips"/number of patients) | Efavirenz + 3 NRTIs (Number of "blips"/number of patients) |
|---|---|---|---|
| 7 days/week | 2/61 | 0/14 | 2/55 |
| 5 days/week | 1/70 | 0/29 | 0/40 |
| 4 days/week | 4/123 | 0/48 | 0/6 |
| 3 days/week | 2/93 including 1 failure | 0/18 | 0/6 |
| 2 days/week | 4/34 including 1 failure | 0/10 | 0/10 |

Thus, it is clear from this study that, contrary to the predominant prejudice, the number of administrations of the quadruple therapies according to the invention (3 NRTIs combined with 1 NNRTI) can be limited to two administrations per week without leading to a resumption of HIV replication, in inverse proportion to the pressure exerted daily by the combination in question.

In fact, to the extent that the incidence of "blips" can be interpreted as reflecting the replicative activity of the HIV incubating in the patients receiving the best treatment below the detection thresholds, this should increase when the antiviral pressure decreases—either because the antiviral combination is no longer powerful enough on a daily basis, or because the administrations of antivirals are irregularly spaced in the week. Now, that is certainly not so.

Moreover, in the patients treated with the quadruple therapy combining nevirapine, didanosine, emtricitabine and tenofovir, no failure and no "blip" was recorded during 120 dosages carried out in 7 patients thus treated, each for an average of 18 months (554 weeks), at a rate of: five days per week (3 patients and 110 cumulative weeks), or four days (3 patients and 270 weeks of treatment), or three days (3 patients and 137 weeks), or 2 days per week (2 patients and 36 weeks of intermittent antiviral treatment).

In contrast, in the 53 patients treated with Atripla or equivalent seven days per week as recommended, for an average duration of 121 weeks, the incidence of "blips" was 10 out of 450 dosages.

Example 8

The number of viral breakthroughs was measured in the patients treated with the quadruple therapies according to the invention.

Three quadruple therapies were tested in this way:
quadruple therapy 1 (Q1): nevirapine, emtricitabine, tenofovir and didanosine;
quadruple therapy 2 (Q2): etravirine, emtricitabine, tenofovir and didanosine; and
quadruple therapy 3 (Q3): efavirenz, emtricitabine, tenofovir and didanosine.

The results obtained are presented in the following table.

| Treatment | Q1 | Q2 | Q3 |
| --- | --- | --- | --- |
| 2 days/week | 0/10 | 0/2 | 0/8 |
| 1 day/week | 0/4 | Not tested | 0/3 |

The 18 patients treated with Q1, Q2 and Q3 had a cumulative 860 weeks of treatment, whereas the 7 patients treated with Q1 and Q3 had a cumulative 143 weeks of treatment.

Thus, 22 patients were treated with a quadruple therapy according to the invention for two days per week (22 patients) or one day per week (7 patients out of 22) for a total duration of more than 1000 treatment-weeks, or almost 20 patient-years, without any viral breakthrough being detected, apart from a single isolated and transient "blip", even though more than 210 assays of plasma HIV viremia were carried out.

Thus, it is clear from this study that, contrary to the predominant prejudice, the number of administrations of the quadruple therapies according to the invention (3 NRTIs combined with 1 NNRTI) can be limited to one or two administrations per week without leading to viral breakthrough.

The invention claimed is:

1. A pharmaceutical composition for treating the human immunodeficiency virus (HIV) in human beings comprising four active principles selected as being:
    a non-nucleoside inhibitor of reverse transcriptase (NNRTI) selected from nevirapine, efavirenz and etravirine;
    a nucleoside inhibitor of reverse transcriptase (NRTI) selected from lamivudine or emtricitabine; and
    two different nucleoside or nucleotide inhibitors of reverse transcriptase (NRTI): didanosine and tenofovir.
2. The pharmaceutical composition as claimed in claim 1, wherein the NNRTI is nevirapine or etravirine.
3. The pharmaceutical composition as claimed in claim 2, wherein the NNRTI is nevirapine.
4. The pharmaceutical composition as claimed in claim 1, wherein one of the NRTIs is emtricitabine.
5. The pharmaceutical composition as claimed in claim 1, wherein it comprises, as active principles, nevirapine, emtricitabine, tenofovir and didanosine.
6. The pharmaceutical composition as claimed in claim 5, wherein it comprises 400 mg of nevirapine, 200 mg of emtricitabine, 245 mg of tenofovir and 250 mg of didanosine.
7. The pharmaceutical composition as claimed in claim 3, for treating pregnant women.
8. The pharmaceutical composition as claimed in claim 1, for daily administration one to six days per week.
9. The pharmaceutical composition as claimed in claim 8, for daily administration one to four days per week.
10. A pharmaceutical composition according to claim 1 comprising:
    a non-nucleoside inhibitor of reverse transcriptase (NNRTI); and
    three nucleoside or nucleotide inhibitors of reverse transcriptase (NRTI)
    as a combination product for simultaneous, separate or spread over time administration for treating HIV in a human being.
11. The pharmaceutical composition as claimed in claim 10, being in the form of a unit dosage form containing nevirapine and didanosine, and a unit dosage form containing emtricitabine and tenofovir.
12. The pharmaceutical composition as claimed in claim 10, being in the form of a unit dosage form containing efavirenz and didanosine, and a unit dosage form containing emtricitabine and tenofovir.

* * * * *